United States Patent [19]
Larsen et al.

[11] Patent Number: 6,008,421
[45] Date of Patent: Dec. 28, 1999

[54] PRODUCTION OF $^{11}$C-METHYL IODIDE

[76] Inventors: Peter Larsen, Ravnehusvej 1 DK-3500, Vaerlöse, Denmark; Martin Orbe, Granitvägen 24E S-752 43, Uppsala, Sweden; Kent Dahlström, Svankärrsvägen 15A S-756 53, Uppsala, Sweden; Johan Ulin, Krongatan 37, S-752-38, Uppsala, Sweden

[21] Appl. No.: 08/836,606

[22] PCT Filed: Oct. 20, 1995

[86] PCT No.: PCT/SE95/01247

§ 371 Date: Aug. 21, 1997

§ 102(e) Date: Aug. 21, 1997

[87] PCT Pub. No.: WO96/15086

PCT Pub. Date: May 23, 1996

[30] Foreign Application Priority Data

Nov. 14, 1994 [SE] Sweden ................................ 9403913-8

[51] Int. Cl.$^6$ ................................ C07C 17/10; F28D 7/00
[52] U.S. Cl. ........................... 570/255; 422/159; 422/198
[58] Field of Search ............................ 570/255; 422/159, 422/198

[56] References Cited

U.S. PATENT DOCUMENTS 5,334,788   8/1994   Baucom et al. ........................ 570/175

*Primary Examiner*—Alan Siegel
*Attorney, Agent, or Firm*—Young & Thompson

[57] ABSTRACT

The present invention discloses a method and an apparatus for high yield production of $^{11}$C-methyl iodide by selectively monohalogenating $^{11}$C-methane, whereby the method is comprising a first step of introducing $^{11}CH_4$ into an apparatus containing a circulation system comprising a number of connected circulation members (1–7), and the circulation system is further comprising a number of valves (V114 V5) and at least one pump (8) for controlling the circulation. The method further comprises a second step of recirculation of $^{11}CH_4$ and introduction of iodine vapor into the circulating gas stream passed through a heated reaction chamber (3) within the apparatus having the circulation system during a predefined time period during continuous removal of formed $^{11}CH_3I$ by means of a second trap (7), and a third step of releasing after the predefined time period the produced $^{11}$C-methyl iodide for further processing by heating the second trap (7) containing the produced $^{11}CH^3I$ while leading a stream of inert gas through the second trap, whereby this second trap (7) will act as a small size chromatograph purifying the desired $^{11}CH_3I$.

20 Claims, 2 Drawing Sheets

PRODUCTION OF $^{11}$C-METHYL IODIDE

This application is a 371 of PCT/SE95/01247 filed Oct. 20, 1995.

TECHNICAL FIELD

The present invention relates to a method and a system for production of the positron emitting compound $^{11}$C-methyl iodide in high yields, with good radiochemical purity and high specific activity.

PRIOR ART

A group of medical diagnostic procedures utilize radioactive labeled compounds. This principle is also used for the diagnostic procedure PET (Positron Emitting Tomography), where the radioactive atoms are positron emitters. Some examples of positron emitting elements include nucleids of carbon (C), oxygen.(O), nitrogen (N) or fluorine (F). These elements are the backbone of almost all biological active compounds. To be able to use the method stable isotopes are replaced with a radioactive isotope. The radioactive labeled compounds, called tracers, are transported, accumulated and converted exactly the same way as for the non-radioactive compound. The PET method has possibilities to detect malfunction on a cellular level in the investigated tissues or organs. The method is very sensitive and requires only nanomole quantities of produced radioactive tracers. The half-life of these radioactive tracers range from 2 to 110 minutes and the production of the radioactive nucleids as well as the biological active tracer has to take place just prior to the use of it. The radioactive nucleids are produced in an accelerator and immediately processed to small molecules. These small molecules react with larger non-radioactive building blocks to yield the desired tracer.

One important and very useful starting compound is carbon-11 labeled methyl iodide ($^{11}$C—CH$_3$I). Carbon is the most frequent type of atom in biological active compounds and pharmaceuticals. With $^{11}$C-labeled methyl iodide it is possible to make a large variety of $^{11}$C-labeled compounds. These are of interest for diagnosis and follow up of a treatment of, for example, cancer, epilepsy or dementia.

Such a compound is today most often formed from $^{11}$C-labeled carbon dioxide ($^{11}$CO$_2$) through reduction with lithium aluminum hydride (LAH) to $^{11}$C-labeled methanol and a reaction of this compound with hydrogen iodide to produce $^{11}$C-labeled methyl iodide. The reaction takes place in an organic solvent. This method has several disadvantages; the chemicals are cumbersome to use which makes the process unreliable and the LAH contains a variable amount of cold carbon dioxide lowering the relation between produced radioactive and non-radioactive $^{11}$C-labeled methyl iodide. In many investigations is it desirable to have a high ratio.

Another way to produce this compound is the halogenation of $^{11}$C-labeled methane ($^{11}$CH$_4$) with iodine. The $^{11}$CH$_4$ is formed from the catalytic reduction of $^{11}$C-labeled carbon dioxide. The halogenation reaction of the $^{11}$CH$_4$ is a nonselective radical reaction taking place under elevated temperatures. As iodine always will be present in a large excess it is difficult to prevent polyhalogenation, leading to low radiochemical purity. In the published literature mixtures between mono-, di-, tri- and tetra-iodinated methane are formed (LIT REF). If the reaction conditions are suitable for formation of only the mono-halogenated compound in high purity, the yields are low (<10%) due to the very short reaction time necessary to prevent further halogenation.

DISCLOSURE OF THE INVENTION

The present invention solves the problem of the low chemical yields and low radio chemical purity of the radical iodination reaction. The reaction time and temperature are optimized to give a pure mono-halogenated methyl iodide. The small fraction of formed $^{11}$C-labeled methyl iodine is removed from the gas mixture, and the remaining $^{11}$C-labeled methane is purified and recirculated. Fresh iodine is added and the process is repeated until the conversion of the $^{11}$CH$_4$ is complete.

According to a first object of the present invention a method for production of $^{11}$C-methyl iodide is disclosed by selectively monohalogenating $^{11}$C-methane, whereby the method is comprising a first step of introduction of $^{11}$CH$_4$ into a circulation system comprising a number of connected circulation members, and the circulation system is further comprising a number of valves and at least one pump for controlling the circulation, a second step of recirculation of $^{11}$CH$_4$ and introduction of iodine vapors into the circulating gas stream passed through at least one heated reaction chamber within the circulation system during a predefined time period during continuous removal of formed $^{11}$CH$_3$I by means of the second trap, and a third step of releasing the produced $^{11}$C-methyl iodide after the predefined time period for further processing by heating the second trap containing the produced $^{11}$CH$_3$I while leading a stream of inert gas through the second trap, whereby this second trap will act as a small size chromatograph purifying the desired $^{11}$CH$_3$I.

According to a second object of the present invention an apparatus for production of $^{11}$C-methyl iodide is disclosed by selectively monohalogenating $^{11}$C-methane, whereby the apparatus for application of the method is comprising a recirculation system including a first trap, an iodine chamber, at least one heated reaction chamber, a condensation chamber and a trapping chamber, a second trap and at least one pump, whereby the recirculation system further is comprising a number of valves for controlling the circulation and the second trap by means of a suitable contained material, or being a cold trap, will with a high yield trap and store the produced $^{11}$C-methyl iodide to be released for further processing by heating this second trap containing the produced $^{11}$CH$_3$I.

Further embodiments of the method and the apparatus for utilizing the method are additionally defined by the dependent claims 2–6 and 9–12, respectively, in the attached set of claims.

BRIEF DESCRIPTION OF THE DRAWINGS

The invention will be described by preferred embodiments to be contemplated with reference to the accompanying drawings wherein like reference numerals are used throughout to designate like parts. In the drawings.

DESCRIPTION OF EXEMPLIFYING EMBODIMENTS

Figure 1:
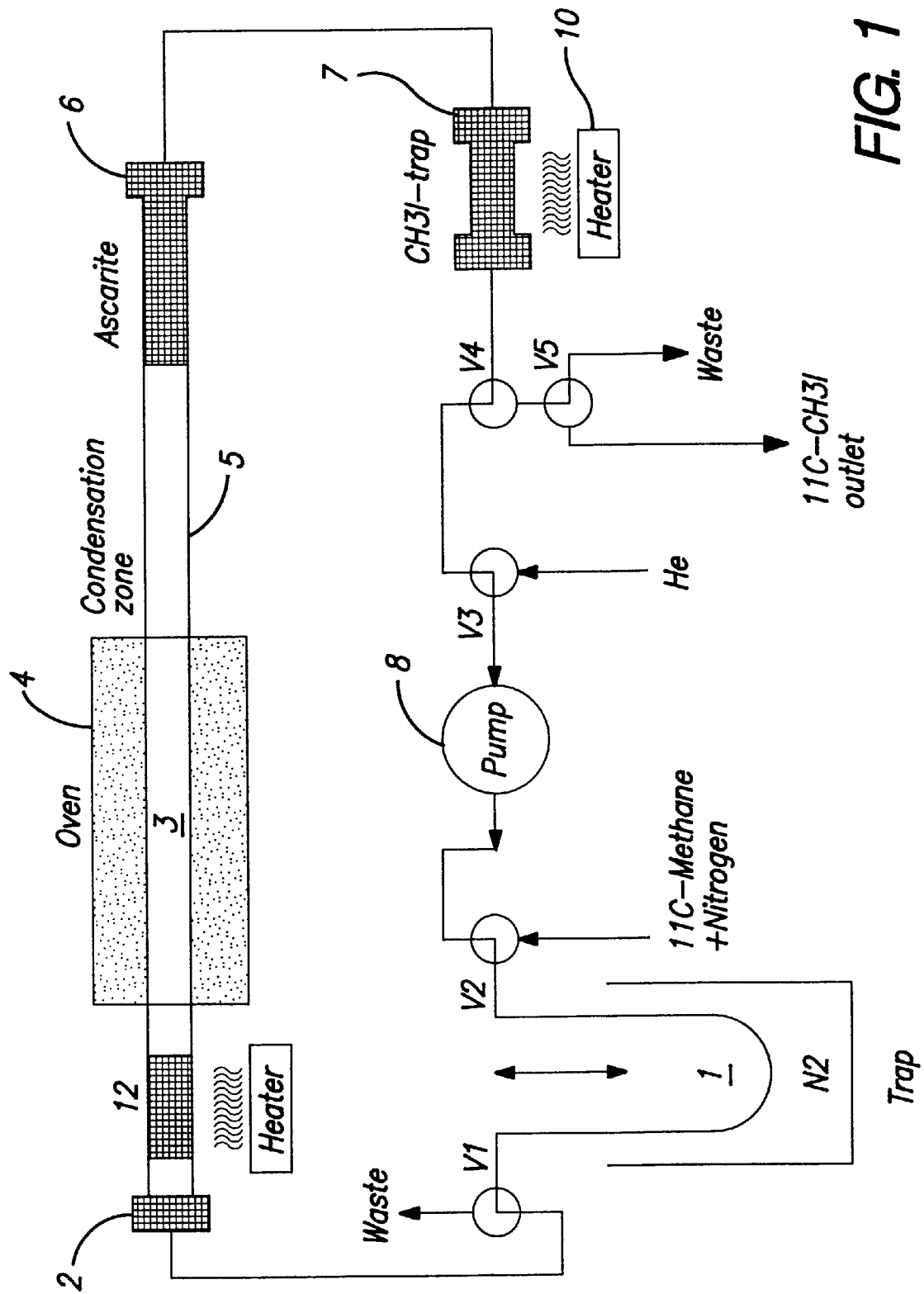
FIG. 1 shows an embodiment of a system including a $^{11}$C-methane source in the recirculation system and utilizing the method according to the present invention.

FIG. 1 demonstrates a first embodiment of an apparatus for performing the process according to the present invention. The apparatus of FIG. 1 contains a closed recirculation circuit comprising a trap 1, for example a cold trap or a molecular sieve trap, as a source of $^{11}$C-methane+nitrogen which is included in the circuit through two valves V1 and V2, respectively. Instead of nitrogen any other inert gas may be utilized. Additionally in the closed circuit there is an iodine source 2, a reaction chamber 3, a condensation zone 5, an ascarite trap 6, a CH$_3$I-trap 7 and a pump 8. The iodine source 2 is a quartz tube where iodine vapors are created by suitable heating of iodine crystals. The reaction chamber 3 is heated by an oven 4. This chamber 3 may also contain a suitable catalyst for the reaction producing $^{11}$C-methyl iodide by selectively monohalogenating $^{11}$C-methane. After the chamber 3 there is a condensation zone 5, to retrieve into solid form iodine vapors not consumed by the process in the reaction chamber 3. After the condensation zone 3 there is a trap 6 which in a preferred embodiment is containing ascarite and where HI, $^{11}$CO$_2$ and the rest of the iodine will be trapped. After the trap 6 there is another trap which adapted to remove and store the produced methyl iodide from the recirculating gas. The recirculation of gas in the system is achieved by means of at least one pump. Between the second trap 7 and a pump 8 there are additional valves V3, V4 and V5. Valves V4 and V5 may be switched to let out produced and stored $^{11}$C-methyl iodide from the trap 7. Valve V3 is used for adding inert gas, for example helium, into the system as will be discussed below.

Figure 2:
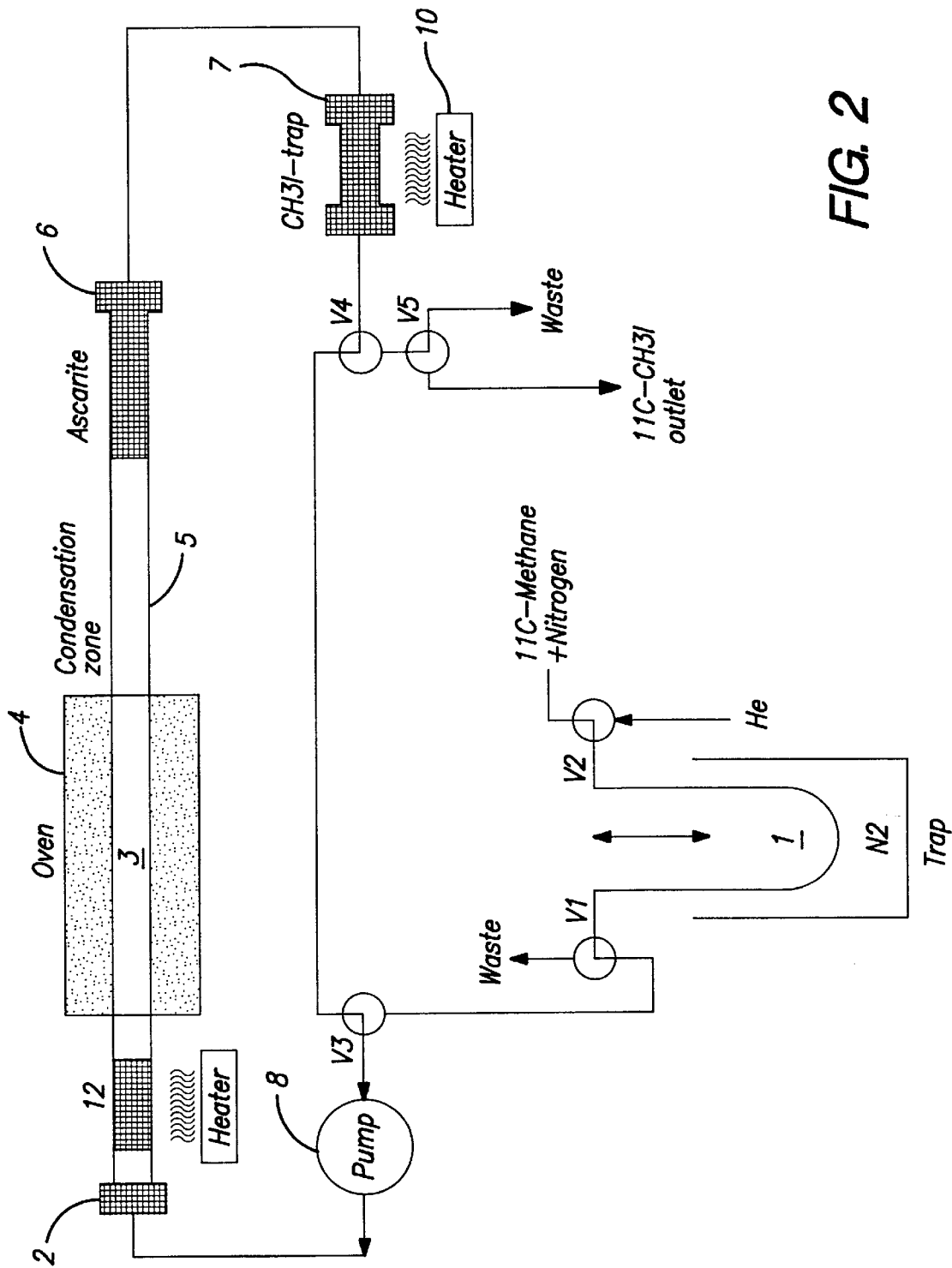
FIG. 2 shows an other embodiment of a system having to the recirculation system an external $^{11}$C-methane source and utilizing the method according to the present invention.

In FIG. 2 is demonstrated in a second embodiment an alternative apparatus for performing the process according to the present invention. The apparatus of FIG. 2, similar to the apparatus of FIG. 1, contains a trap 1, for example a cold trap or a molecular sieve trap, an iodine source 2, a reaction chamber 3, a condensation zone 5, an ascarite trap 6, a CH3I-trap 7 and a pump 8. The difference from FIG. 1 is that the trap 1 is not a part of the recirculation system, but the closed circulation is achieved by means of switching open the passage between valves V4 and V3. In the apparatus of FIG. 2 the inert gas like helium is inserted through valve V2, while in FIG. 1 the inert gas is inserted through valve V3. In the apparatus of FIG. 2 all valves V1, V2, V3, V4, and V5 are placed between the second trap 7 and the pump 8. In both embodiments of FIG. 1 and FIG. 2 when the trap 1 is a cold trap it is preferably cooled by means of a liquid having a boiling point of below –162° C. The second trap 7 may be heated by a heater 10 for release of trapped CH3I via valves V4 and V5. Valve V5 is used to direct the output either as a waste or as output of the desired product.

The procedure according to the present invention for production of $^{11}$C-methyl iodide by selectively monohalogenate $^{11}$C-methane may be divided into three step as described below.

Step 1: Introduction of $^{11}$CH$_4$ into the Recirculation System

It is essential to the synthesis that the system is loaded with pure $^{11}$CH$_4$ in a pure inert gas.

$^{11}$CH$_4$ in N$_2$ could be produced in the target by irradiation of a mixture of N$_2$ and H$_2$ with photons, or the $^{11}$CH$_4$ could be produced outside the target by catalytic or non catalytic reduction of $^{11}$CO$_2$ or $^{11}$CO in N$_2$.

The purification and concentration of the $^{11}$CH$_4$ is done by leading the gas mixture through a trap 1 filled with Porapak N. and cooled in liquid N$_2$ (FIG. 1 and 2). In this trap 1 the methane is retained and the impurities are swept through. After the trapping the $^{11}$CH$_4$ is released into a stream of helium, He, by moving the trap from the cooling bath. If the trap 1 is placed inside the recirculating part of the system (FIG. 1) the $^{11}$CH$_4$ is now in place and the recirculation can begin. If the trap is placed outside the recirculating part of the system (FIG. 2) the $^{11}$CH$_4$ is loaded into the system through valves V1 and V3 in a small volume of, for instance, He.

As an alternative for helium, He, may be substituted any other inert gas like Ne, Ar, Kr, Xe or another gas as for example N$_2$.

The cooling of a cold trap may utilize liquid nitrogen, liquid air, liquid oxygen or liquid He, Ne, Ar, etc., or solid CO$_2$, a cooling compressor, a vortex tube, or the like.

In an alternative embodiment instead of using a cold trap, the $^{11}$CH$_4$ could be trapped at a higher temperature (room temperature) an be released by heating. The Porapak N could be substituted by a large number of trapping materials. Examples of such materials are: Activated carbon, molecular sieves, a large number of GC packing material, plastic powder, polymers or inorganic carriers coated with high boiling liquids, or carriers coated with chemically bonded organic molecules, and so on.

Instead of using a cold trap to capture $^{11}$CH$_4$, $^{11}$CO$_2$ produced by irradiation of N$_2$ containing traces of O$_2$ by protons, can be captured in a trap containing a mixture of molecular sieve and a catalyst (Ni, Pd, Pt, Rh, Fe, . . . ) saturated with H$_2$. The trap is then flushed with inert gas, closed and heated. The $^{11}$CO$_2$ is released from the molecular sieve and reduced to $^{11}$CH$_4$ by the hydrogen, H$_2$ on the catalyst. The trap is opened and the $^{11}$CH$_4$ is released into a stream of inert gas.

If the trap is now placed inside the circulating part of the system (FIG. 1) the $^{11}$CH$_4$ is now in place and the recirculation can start.

If the trap is placed outside the circulating portion of the system (FIG. 2) the $^{11}$CH$_4$ is loaded into the system through a valve V1 and V3 in a small volume of inert gas.

Step 2: Recirculation of $^{11}$CH$_4$ During Continuous Removal of Formed $^{11}$CH$_3$I.

All valves are switched such that the pump circulates the mixture of $^{11}$CH$_4$ and for instance He from the trap 1 into the quartz tube 2 where it is mixed with iodine vapors from the heated iodine crystals. The gas mixture is then led through a piece of quartz tube 3 heated to of the order 720° C. by means of an electrical oven 4, whereby the iodination of methane takes place.

After the oven the gases pass a piece of quartz tube (condensation zone 5) kept at room temperature, i.e. about 20° C., where most of the excess of iodine crystallizes and then a piece of tube 6 filled with ascarite where impurities, mainly HI, $^{11}$CO$_2$ and the rest of the iodine, will be trapped. The $^{11}$C-methyl iodine is trapped in the CH$_3$I-trap and the unchanged $^{11}$CH$_4$ will be recirculated.

The pump 8 used for circulation, which may be any type of suitable device, e.g., a membrane pump, rotary vane pump, piston pump, gear pump, Roots pump screw pump, peristaltic pump, or the like, could in practice be placed anywhere in the closed circuit.

The I$_2$-chamber 2, the reaction chamber 3, the condensation zone 5 and the ascarite chamber 6 is in the preferred embodiment typically placed in a single piece of quartz tube, but could also be separate chambers manufactured from different materials and connected to each other by means of tubes or hoses.

The reaction chamber should be chemically inert and able to withstand the temperature needed to convert $^{11}$CH$_4$ to CH$_3$I (200–1000° C.). It could be made from quartz, metals, alloys or ceramics. It is heated by an electrical oven, a flame or a stream of hot air. It is empty or filled with a material that catalyses the reaction between $^{11}$CH$_4$ and I$_2$.

The condensation zone 5 can be kept at room temperature, or cooled to +20 to –100° C. by a stream of cold air, a vortex tube or any other cooling device.

The Ascarite in the Ascarite chamber 6 may be replaced by Sb, Na$_2$SO$_3$, or strong bases such as KOH or Ca(OH)$_2$.

In the preferred embodiment the $CH_3I$-trap 7 is typically filled with Porapak N. The trapping is carried out at room temperature, and the release is carried out by heating to 190° C. by means of an electrical oven 10 or by a stream of hot air. This Porapak N may be substituted by a large number of trapping materials. Examples of such materials are: Activated carbon, molecular sieves, a large number of GC packing material, plastic powder, polymers or inorganic carriers coated with high boiling liquids, or carriers coated with chemically bonded organic molecules, and so on. The $CH_3I$-trap 7 may as well be designed as a cooling trap containing for example solid $CO_2$ in ethanol or acetone.

The trapping and release could take place between −250 and +300° C.

Step 3: Release and Purification of Trapped $^{11}CH_3I$.

The $^{11}CH_3I$ is released by heating the trap 7, while leading a stream of helium through system and the trap. Depending on the trapping material used, the trap will act as a small size chromatograph. This effect can be used to get a pure product by using V5 (FIG. 1 and 2) to collect the $^{11}CH_3I$ fraction.

The method and apparatus involving recirculation of $^{11}CH_4$ mixed for example with helium during continuous removal of formed $^{11}CH_3I$ has yield which is very much higher compared to prior art technique. The time for the recirculation process will for example be dependent of the capacity of the pump 8, but a time of about 20 second is typical in the preferred embodiment.

We claim:

1. Method of production of $^{11}C$-methyl iodide by selectively monohalogenate $^{11}C$-methane, comprising the steps of introduction of $^{11}CH_4$ into a circulation system including a number of connected circulation members, said circulation system further comprising a number of valves means (V1–V5) and at least one pump means (8) for controlling the circulation, recirculation of $^{11}CH_4$ and introduction of iodine vapors to the recirculating gas stream passed through at least one heated reaction chamber means (3) within said circulation system during a predefined time period during continuous removal of formed $^{11}CH_3I$ by means of second trapping means (7) containing a suitable material for trapping of $CH_3I$, release of the produced $^{11}C$-methyl iodide after said predefined time period for further processing by heating said second trapping means (7) containing the produced $^{11}CH_3I$ while leading a stream of inert gas through said second trapping means (7).

2. Method according to claim 1, characterized in that said second trapping means (7) during the release of the produced $^{11}CH_3I$ is acting as a small size chromatograph purifying the desired $^{11}CH_3I$.

3. Method according to claim 1, characterized in that an iodine chamber means (2) produces vapor of iodine by means of heating iodine crystals in said iodine chamber means.

4. Method according to claim 3, characterized in that a trapping chamber means (6) is trapping impurities, mainly HI, $^{11}CO_2$ and the rest of the iodine in the circulating gas after passing the condensation chamber means (6).

5. Method according to claim 1, characterized in that a first trapping means (1) is prepared in advance of the recirculation process by being flushed with inert gas, closed and heated, whereby $^{11}CO_2$ is released from a molecular sieve or a cold trap and is reduced to $^{11}CH_4$ by the $H_2$ on a catalyst after which said first trapping means is opened and $^{11}CH_4$ is released into a stream of inert gas in said recirculation system for production of $^{11}C$-methyl iodide to be trapped in said second trapping means (7).

6. Method according to claims 1, characterized in that a first trapping means (1) is prepared before starting the recirculation process by being flushed with inert gas, closed and heated, whereby $^{11}CO_2$ is released from a molecular sieve or a cold trap and is reduced to $^{11}CH_4$ by the $H_2$ on a catalyst after which said first trapping means is opened and $^{11}CH_4$ is released into a stream of inert gas in said recirculation system for production of $^{11}C$-methyl iodide to be trapped in said second trapping means.

7. Method according to claim 2, characterized in that an iodine chamber means (2) produces vapor of iodine by means of heating iodine crystals in said iodine chamber means.

8. Method according to claim 7, characterized in that a trapping chamber means (6) is trapping impurities, mainly HI, $^{11}CO_2$ and the rest of the iodine in the circulating gas after passing the condensation chamber means (6).

9. Method according to claim 2, characterized in that a first trapping means (1) is prepared before starting the recirculation process by being flushed with inert gas, closed and heated, whereby $^{11}CO_2$ is released from a molecular sieve or a cold trap and is reduced to $^{11}CH_4$ by the $H_2$ on a catalyst after which said first trapping means is opened and $^{11}CH_4$ is released into a stream of inert gas in said recirculation system for production of $^{11}C$-methyl iodide to be trapped in said second trapping means.

10. Method according to claim 3, characterized in that a first trapping means (1) is prepared before starting the recirculation process by being flushed with inert gas, closed and heated, whereby $^{11}CO_2$ is released from a molecular sieve or a cold trap and is reduced to $^{11}CH_4$ by the $H_2$ on a catalyst after which said first trapping means is opened and $^{11}CH_4$ is released into a stream of inert gas in said recirculation system for production of $_{11}C$-methyl iodide to be trapped in said second trapping means.

11. Method according to claim 4, characterized in that a first trapping means (1) is prepared before starting the recirculation process by being flushed with inert gas, closed and heated, whereby $^{11}CO_2$ is released from a molecular sieve or a cold trap and is reduced to $^{11}CH_4$ by the $H_2$ on a catalyst after which said first trapping means is opened and $^{11}CH_4$ is released into a stream of inert gas in said recirculation system for production of $^{11}C$-methyl iodide to be trapped in said second trapping means.

12. Method according to claim 5, characterized in that a first trapping means (1) is prepared before starting the recirculation process by being flushed with inert gas, closed and heated, whereby $^{11}CO_2$ is released from a molecular sieve or a cold trap and is reduced to $^{11}CH_4$ by the $H_2$ on a catalyst after which said first trapping means is opened and $^{11}CH_4$ is released into a stream of inert gas in said recirculation system for production of $^{11}C$-methyl iodide to be trapped in said second trapping means.

13. Apparatus for production of $^{11}C$-methyl iodide by selectively monohalogenate $^{11}C$-methane, comprising a recirculation system including first trapping means (1), iodine-chamber means (2), heated reaction chamber means (3), condensation chamber means (5) and trapping chamber means (6), second trapping means (7) and pump means (8), said recirculation system further comprising a number of valves (V1–V5) for controlling the circulation, whereby said second trapping means (7) by means of a suitable contained material is trapping and storing the produced $^{11}$C-methyl iodide to be released for further processing by heating said second trapping means (7) containing the produced $^{11}$CH$_3$I.

14. Apparatus for production of $^{11}$C-methyl iodide by selectively monohalogenate $^{11}$C-methane, comprising a recirculation system including first trapping means (1), iodine-chamber means (2), heated reaction chamber means (3), condensation chamber means (5) and trapping chamber means (6), second trapping means (7) and pump means (8), said recirculation system further comprising a number of valves (V1–V5) for controlling the circulation, whereby said second trapping means (7) is a cold trap trapping and storing the produced $^{11}$C-methyl iodide to be released for further processing by heating said second trapping means (7) containing the produced $^{11}$CH$_3$I.

15. Apparatus according to claim 13, characterized in that said iodine chamber means (2) produces vapor of iodine by heating of iodine crystals in said iodine chamber means.

16. Apparatus according to claim 15, characterized in that said trapping chamber means (6) is trapping HI, $^{11}$CO$_2$ and the rest of the iodine in the circulating gas after passing said condensation chamber means (5).

17. Apparatus according to claim 16, characterized in that said first trapping means (1) is containing a suitable trapping material for $^{11}$CH$_4$, e.g. activated carbon, molecular sieves, a GC packing material, plastic powder, polymers or inorganic carriers coated with high boiling liquids, or carriers coated with chemically bonded organic molecules.

18. Apparatus according to claim 16, characterized in that said first trapping means (1) is a cold trap.

19. Apparatus according to claim 14, characterized in that said iodine chamber means (2) produces vapor of iodine by heating of iodine crystals in said iodine chamber means.

20. Apparatus according to claim 19, characterized in that said trapping chamber means (6) is trapping HI, $^{11}$CO$_2$ and the rest of the iodine in the circulating gas after passing said condensation chamber means (5).

* * * * *